United States Patent
Barton et al.

(10) Patent No.: US 11,255,764 B2
(45) Date of Patent: Feb. 22, 2022

(54) DEVICE AND METHOD FOR TESTING THE LIFT OF ROOF TILES

(71) Applicant: Rimkus Consulting Group, Inc, Deerfield Beach, FL (US)

(72) Inventors: Daniel P. Barton, Tampa, FL (US); Michael M Powell, Tampa, FL (US); Jordan T Fox, Tampa, FL (US); Michael C Carnicom, Tampa, FL (US)

(*) Notice: Subject to any disclaimer, the term of this patent is extended or adjusted under 35 U.S.C. 154(b) by 104 days.

(21) Appl. No.: 16/809,885

(22) Filed: Mar. 5, 2020

(65) Prior Publication Data

US 2021/0278329 A1    Sep. 9, 2021

(51) Int. Cl.
*G01N 3/08*    (2006.01)
*G01N 3/06*    (2006.01)

(52) U.S. Cl.
CPC .............. *G01N 3/08* (2013.01); *G01N 3/062* (2013.01); *G01N 3/066* (2013.01); *G01N 3/068* (2013.01); *G01N 2203/0017* (2013.01)

(58) Field of Classification Search
CPC .......... E02D 33/00; G01N 3/08; G01N 3/062; G01N 3/066; G01N 3/068; G01N 2203/0017

USPC .......................................................... 73/826
See application file for complete search history.

(56) References Cited

U.S. PATENT DOCUMENTS

| | | | |
|---|---|---|---|
| 4,135,393 A | 1/1979 | Jordan | |
| 4,907,458 A * | 3/1990 | Biggs | G01N 19/04 73/827 |
| 5,067,353 A * | 11/1991 | Sersen | G01N 3/20 73/849 |
| 5,461,929 A * | 10/1995 | Jordan | G01L 5/06 73/828 |
| 6,880,412 B1 | 4/2005 | Gupta | |
| 8,776,610 B2 | 7/2014 | Cummings et al. | |
| 2006/0137476 A1* | 6/2006 | Bull | G01L 5/102 73/862.393 |

FOREIGN PATENT DOCUMENTS

JP    2002148151    *    5/2002

* cited by examiner

*Primary Examiner* — Octavia Hollington

(57) ABSTRACT

The invention relates to uplift testing apparatus and method used to provide a quality control test to confirm adequate bonding by the mortar or adhesive to the tile and underlayment or mechanically attached tile roof systems, and, more particularly it is a direct tensile load that is applied by pulling up on the edge of the tile by using a tile testing scale.

9 Claims, 5 Drawing Sheets

DEVICE AND METHOD FOR TESTING THE LIFT OF ROOF TILES

BACKGROUND OF THE INVENTION

1) Field of the Invention

The invention relates to an uplift testing apparatus and method used to provide a quality control test to confirm adequate bonding by the mortar, adhesive, or mechanical fasteners used to affix a roofing tile to the roofing substrate, and, more particularly it applies a direct tensile load by pulling up on the edge of the tile with a digitally measured vertical uplifting force and simultaneously quantifies the amount of lift in accordance with Testing Application Standard (TAS) 106.

2) Description of Related Art

Testing Application Standard (TAS) 106 is found within the Florida Building Code, and defines the standard procedure for field verification of the bonding of mortar or adhesive set tile systems and mechanically attached, rigid, discontinuous roof systems. The TAS 106 standard is incorporated herein by reference. The specification requires that the test apparatus consist of hook shaped to a 90-degree angle, or other load transfer device capable of sliding underneath the nose of the tile and remaining in place as the upward loads are applied. The hook or other device shall have sufficient strength to resist applied loads of at least 100 lbf, and that the load be displayed within 0.1 lbf. The specification also requires the test to measure the force and the corresponding amount of lift. Since this testing occurs in the field the apparatus must be self-contained and portable.

Additionally, the accepted practice by inspectors includes both photographic recording of testing as well as written documentation.

Currently devices available such as the COM-TEN tile tester do not provide a means of measuring both the uplift force and the displacement distance of the tile using the same portable instrument.

Therefore, what is needed in the art is an apparatus that provides the inspector a portable apparatus that has the ability to measure both uplift force and displacement distance, as well as provide the ability for the inspector to more easily photographically record the testing results.

BRIEF SUMMARY OF THE INVENTION

The invention in one form is directed to a portable apparatus capable of measuring the uplift force and the displacement associated displacement of the roof tile.

The invention in another form provides a method of using the apparatus to capture the uplift force and the associated displacement of the tile.

An advantage of the present invention is to provide a simple, portable testing apparatus capable of being used by an inspector with a single hand allowing them to test the uplift pressure and document associated displacement while recording the test results photographically.

BRIEF DESCRIPTION OF THE DRAWINGS

A further understanding of the nature and advantages of particular embodiments may be realized by reference to the remaining portions of the specification and the drawings, in which like reference numerals are used to refer to similar components. When reference is made to a reference numeral without specification to an existing sub-label, it is intended to refer to all such multiple similar components.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION

The instant invention when used to conduct a roof tile uplift test allows the inspector to measure both the uplift force and uplift distance using one hand which frees the other hand to photographically document the test. This eliminates the requirement for a two-man team when conducting a tile uplift test, one to lift the tile and the other to measure and photograph the test.

The term tile as used refers to concrete, clay, masonry, metal and steel roofing tiles.

The term inspector, human, person are used interchangeably and mean person using the instant invention.

The roof tile has a front nose and a back heel. The back heel is attached to a roof underlayment, while the nose rests atop the lower course of roof tiles. The tile is tested for uplift distress by lifting up on the front nose and measuring the force required to lift the tile and the distance that the tile moves from its at rest position.

Figure 1A:
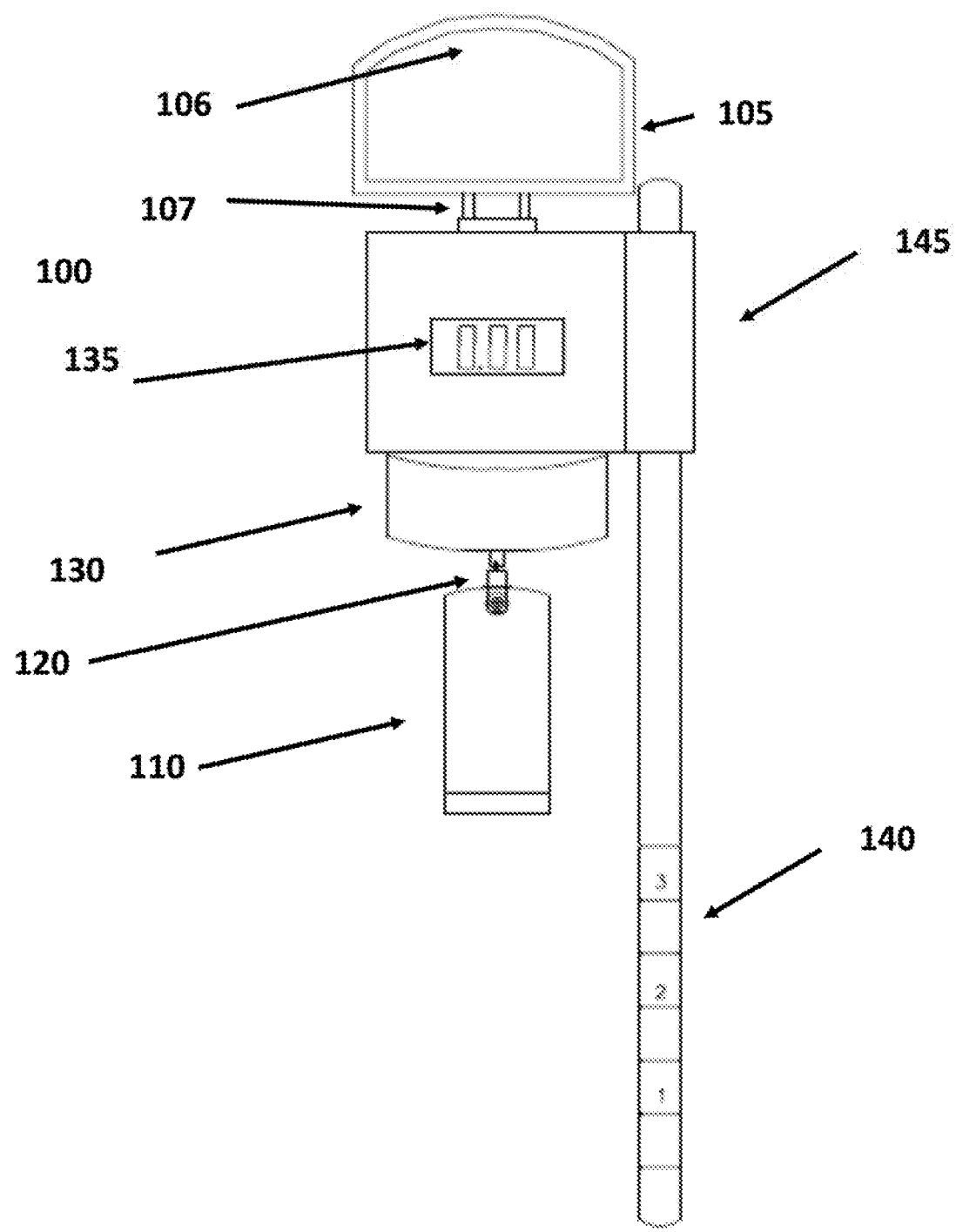
FIG. 1A Front view of the combination uplift testing apparatus, tension load cell and displacement measurement apparatus FIG. 1B Top view of the combination uplift testing apparatus, tension load cell and displacement measurement apparatus FIG. 2. Is an isometric view of the hook FIG. 3 view of tension load cell and displacement measurement display.
Figure 1B:
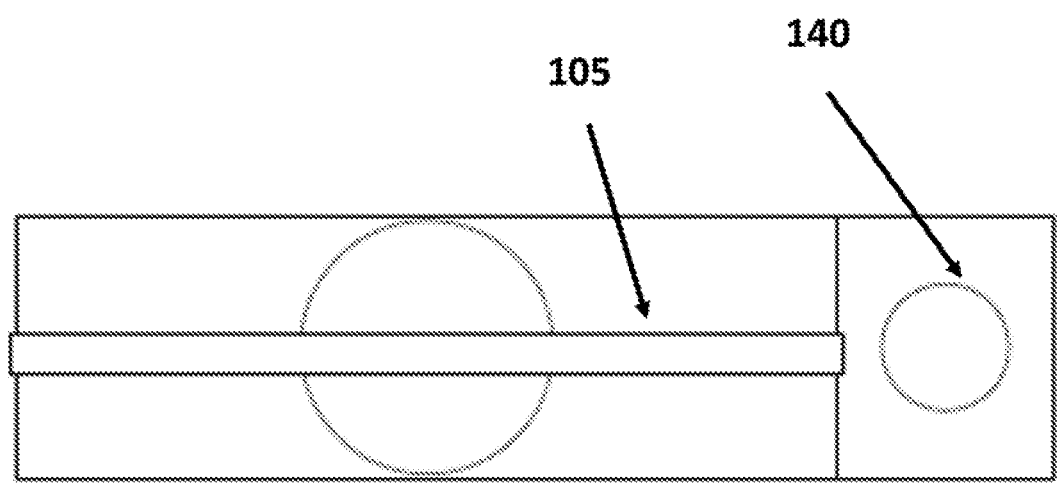
Figure 2:
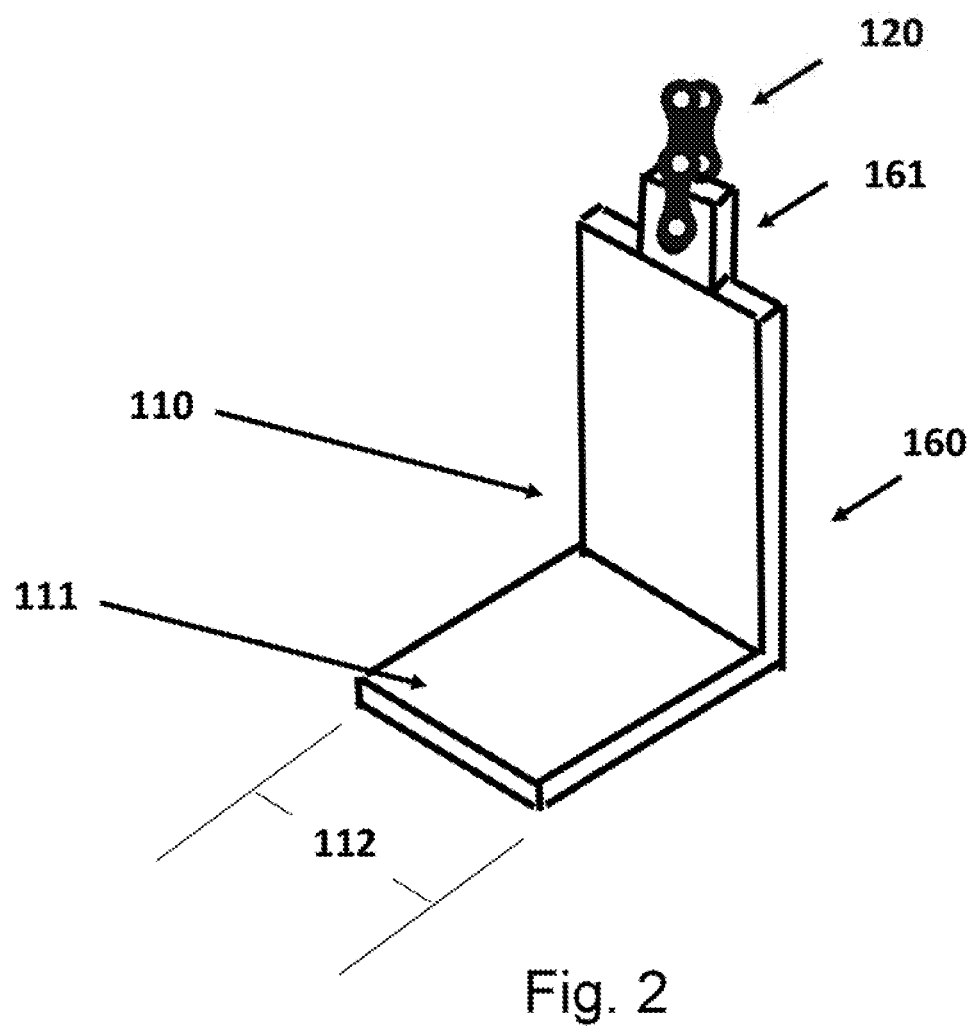
Figure 3:
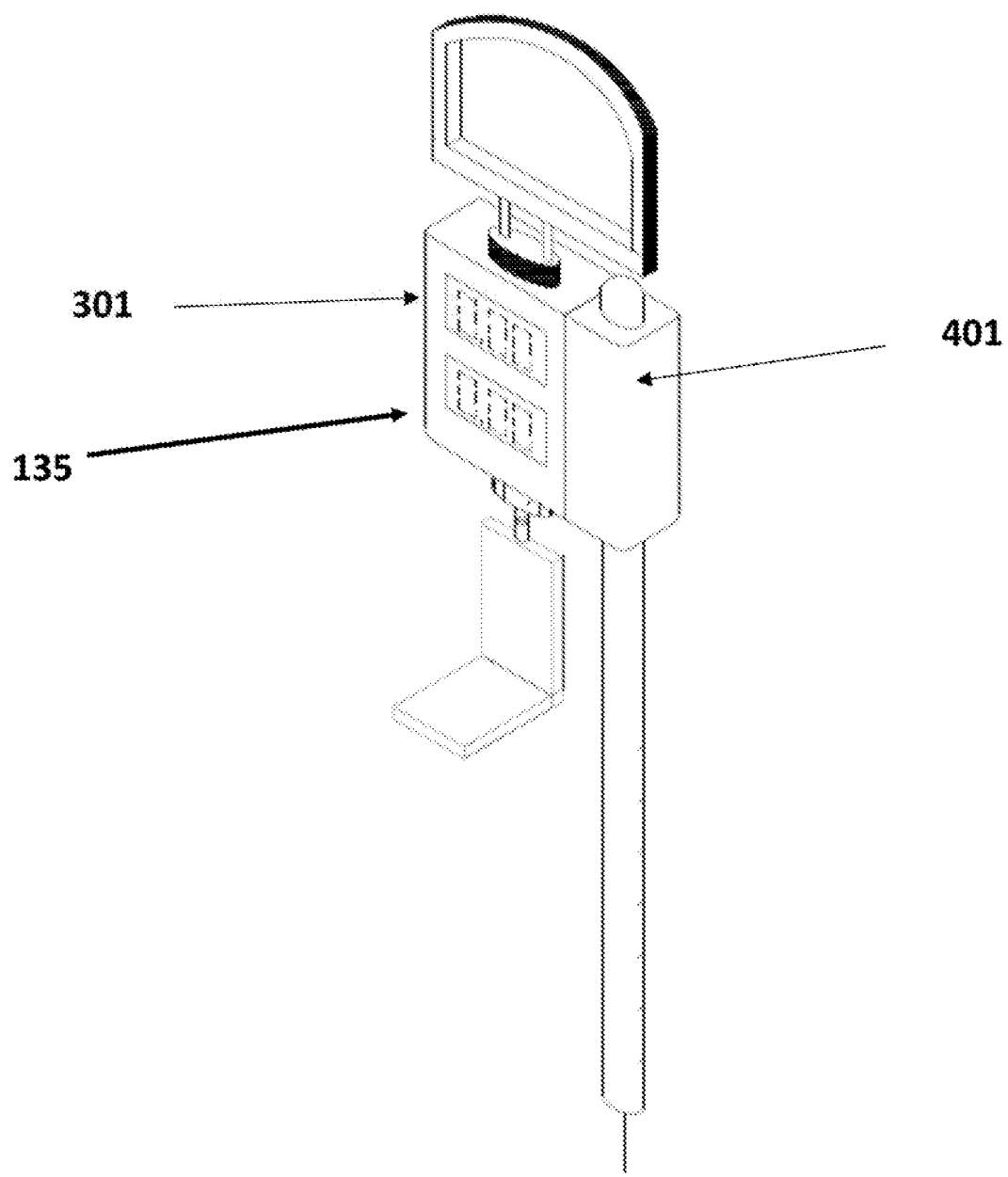
Figure 4:
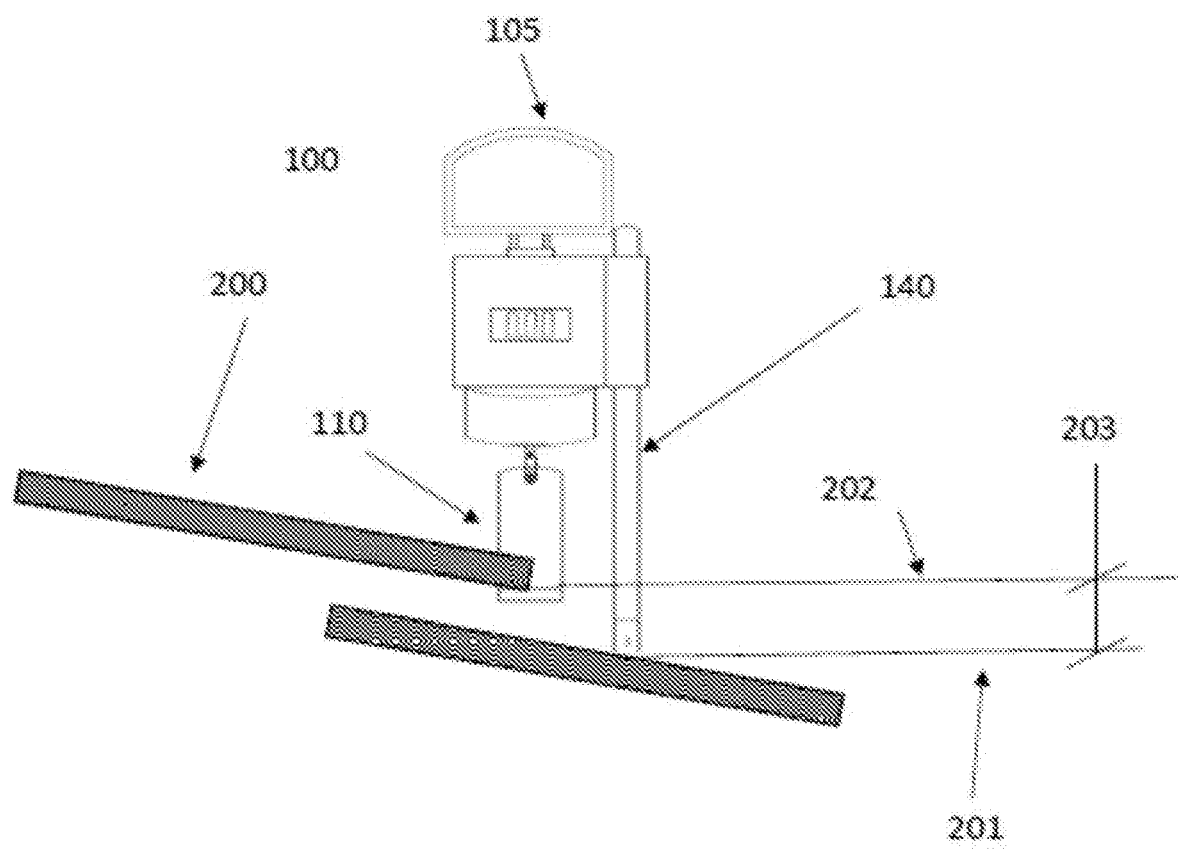
FIG. 4 view of uplift testing apparatus lifting a tile.

Referring now to the drawings, and more particularly to FIGS. 1, 2 and 3, there is shown an uplift testing apparatus 100 of the instant invention comprising of a handle 105, a 90-degree hook or lifting surface 110, connecting chain or link 120, load cell 130, display 135 and displacement scale 140. The load cell 130 can be selected from the group of instruments consisting of spring weight sensors, single point load cell, digital load cell and beam load cell. The 90-degree hook 110 comprised of a hook body 160, hook connector 161 and hook end 111. The hook connector 161 attaches to the connecting cable, chain or link 120 which connects to the load cell 130. The 90-degree hook 110 hook body 160 is designed such that the hook is capable of resisting 100 pounds of force when the load is applied to the end of the hook within 0.25 inches/6.35 mm from the 90-degree hook end 111 and have sufficient width 112 to create a bearing surface so as to minimize damaging the tile. Width 112 has been found to have any dimension from 0.25 inches/6.35 mm to 1.5 inches/38.1 mm. The handle 105 has a grip 106 configured to accept the hand of an inspector and a connector 107 to connect the handle to the load cell 130 to allow up to 360-degree rotation of the handle 105 with respect to the load cell 130. However, a device that provides less functionality can be designed such that handle 105 and grip 106 cannot rotate. The inspector uses the uplift testing apparatus 100 by placing the 90-degree hook 110, so that the 90-degree hook end 111 is under the front 210 of tile 200. Handle 105 is attached to load cell 130 which is attached to the connecting cable, chain or link 120, load cell 130 and 90-degree hook 110. The displacement scale 140 is connected to the load cell 130 and uplift testing apparatus 100 via a slide 145. Preferably the displacement scale 140 is a round bar with lines marked on it indicating the lift distance and sized to freely slide within the slide 145. The line spacing on the displacement scale 140 is preferably ½, 1, 1½, 2 2½, and 3 inches. The handle 105 is attached to the load cell 130 to allow the inspector to view the display 135 and reading the displacement value 301 on displacement scale 140 while lifting the tile 200 by applying force to lift the tile 200 with the handle 105 having a grip 106.

As shown in FIGS. 1A, 1B, 2 and 4 tile 200 is shown with 90-degree hook 110 under the tile. The connecting cable, chain or link 120 is attached to the 90-degree hook 110 and the load cell 130 such that the load cell is capable of measuring the load applied by the inspector to lift the tile 200. The load cell 130 has display 135 which displays the force required to move the tile 200 from rest position 201 to displacement position 202 when the inspector applies the appropriate force to the tile 200 by lifting on handle 105 having a grip 106. The distance represented by the difference in the tile 200 position from rest position 201 to displacement position 202 is lift distance 203. The displacement scale 140 is attached to the uplift testing apparatus 100 using slide 145 such that the displacement scale 140 can provide a measurement of the displacement at the displacement position 202 of the tile 200 from the at rest position 201. Slide 145 and the displacement scale 140 can be made from any material that minimizes binding and allows the displacement scale 140 to freely move as the tile 200 position is moved from rest position 201 to displacement position 202 which is lift distance 203. Typical materials include aluminum, Teflon, nylon, plastic and carbon. The internal shape of the slide 145 can be any shape that allows the displacement scale 140 to slide within the collar 145 as the tile moves from the at rest position 201 to the displacement position 202 of the tile 200. The preferred internal shape is round for the slide 145 but square, rectangular or polygon shapes are applicable. The inspector can read the lift distance 203 from the displacement scale 140.

Alternatively, referring to FIG. 3 the displacement scale can be replaced with a Linear Variable Differential Transformer (LVDT) 401 with a display 301 which displays the distance the tile 200 is lifted when the inspector moves the tile 200 from rest position 201 to displacement position 202 which is lift distance 203 when the inspector applies force to the tile 200 by lifting up on handle 105. This provides the inspector an advantage due to the positioning of the display 135 and display 301 position on the handle 105 so that the inspector can take one picture for the inspection documentation that shows both the applied uplift force and the deflected uplift distance of the tile 200 displacement. The LVDT 401 could be alternatively replaced with a dial indicator, digital dial indicator or calipers.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A portable roof tile testing apparatus for measuring the uplift force and the uplift distance of a roof tile wherein said roof tile comprises: a forward edge which is free to move and a distal edge which is attached to a roof and said-portable roof tile testing apparatus comprises a handle; a 90-degree hook; a connecting link; and a load cell having a scale to read force, wherein said connecting link connects said 90-degree hook to said load cell and a displacement scale is attached to said load cell.

2. The portable roof tile testing apparatus of claim 1 wherein said 90-degree hook comprises a hook body, a hook connector, and a hook tip and said hook tip is configured to lift said roof tile when placed under the forward edge of said roof tile.

3. The portable roof tile testing apparatus of claim 1 wherein the handle comprises a grip configured to accept a hand of an inspector and a connector to connect the handle to the load cell such that said connector allows 360-degree rotation about the connection to said load cell.

4. The portable roof tile testing apparatus of claim 1 wherein the connecting link has a proximal end and a distal end and said connecting link is attached to said load cell on the proximal end of the connecting link and said connecting link is attached to said 90-degree hook at said distal end of said connecting link.

5. The portable roof tile testing apparatus of claim 1 wherein said displacement scale is connected to said load cell to measure said uplift distance of said roof tile when force is applied to said handle and said 90-degree hook tip is placed under said forward edge of said roof tile.

6. The portable roof tile testing apparatus of claim 1 wherein said displacement scale material is selected from the group consisting of aluminum, Teflon, nylon, plastic and carbon.

7. The portable roof tile testing apparatus of claim 1 wherein said displacement scale is selected from the group of instruments consisting of an LVDT a dial indicator, digital dial indicator and calipers.

8. The portable roof tile testing apparatus of claim 1 wherein said load cell is selected from the group of instruments consisting of spring weight sensors, single point load cell, digital load cell and beam load cell.

9. A method of measuring the uplift force and uplift distance of a roof tile wherein said roof tile comprises a forward edge which is free to move and a distal edge which is attached to a roof and using a portable roof tile testing apparatus of claim 1 wherein said 90-degree hook comprises a 90-degree hook body, a 90-degree hook connector, and a hook tip and said method comprising steps of inserting said 90-degree hook tip under said forward edge of said roof tile and lifting said handle such that said roof tile forward edge moves the distance that the roof tile moves from its at rest position to said uplift distance and reading said scale of said load cell to read force and reading said uplift distance on said displacement scale and taking a photograph of said force displayed on said load cell scale and said uplift distance on said displacement scale to photographically record said uplift distance and said force displayed on said load cell scale.

* * * * *